United States Patent [19]
Jacoby

[11] Patent Number: 5,328,483
[45] Date of Patent: Jul. 12, 1994

[54] INTRADERMAL INJECTION DEVICE WITH MEDICATION AND NEEDLE GUARD

[76] Inventor: Richard M. Jacoby, 9951 N. Heather Dr., Castle Rock, Colo. 80104

[21] Appl. No.: 843,282

[22] Filed: Feb. 27, 1992

[51] Int. Cl.$^5$ ............................................. A61M 5/178
[52] U.S. Cl. ..................................... 604/185; 604/195; 604/212; 604/110; 222/213
[58] Field of Search ............... 604/110, 111, 192, 187, 604/194–198, 212, 216, 217, 218, 263; 128/919; 206/364–366; 222/83.5, 213

[56] References Cited

U.S. PATENT DOCUMENTS

| | | | |
|---|---|---|---|
| 2,403,074 | 7/1946 | Goldsmith | 604/198 X |
| 2,667,872 | 2/1954 | Smith | 604/212 X |
| 2,724,384 | 11/1955 | Berthiot | 604/195 |
| 2,935,067 | 5/1960 | Bouet | 604/216 X |
| 3,094,987 | 6/1963 | Dunmire | 604/197 X |
| 3,276,632 | 10/1966 | Stanzel | 222/83.5 |
| 4,645,486 | 2/1987 | Beal et al. | 604/4 |

FOREIGN PATENT DOCUMENTS

| | | | |
|---|---|---|---|
| 0950588 | 9/1949 | France | 604/212 |
| 0334295 | 9/1986 | Italy | 604/192 |

*Primary Examiner*—C. Fred Rosenbaum
*Assistant Examiner*—Mark O. Polutta

[57] ABSTRACT

An intradermal injection device, comprised of a fine gauge injection needle and hub, is enveloped by an attached flexible tear-drop shaped bulb containing a reservoir, and which is itself attached to an integral sliding needle guard. The device contains a prepackaged dose of medication to be administered, which is sealed into the hub and bulb reservoir. Using the hub as a convenient handle, the needle is injected into the skin and the medication is discharged by squeezing the bulb between the thumb and forefinger; afterward the sliding needle guard is deployed by the same squeezing action. A hypodermic injection device, longer needle variation, is accomplished by a modification in the form of an extension to the bulb of a sleeve folding or invaginating over itself, allowing the integral sliding needle guard, when deployed, to extend over the longer needle.

6 Claims, 1 Drawing Sheet

INTRADERMAL INJECTION DEVICE WITH MEDICATION AND NEEDLE GUARD

BACKGROUND OF THE INVENTION

1. Field of the invention

This invention relates in general to the hypodermic injection of medication and specifically to the hypodermic injection of a self contained prepackaged unit dose of medication through a needle with an integral needle guard. Intradermal injection is a subset of the category of hypodermic injections.

2. Description of related art

A common form of hypodermic injection of medication is the intradermal injection. Intradermal injection using a small syringe attached to a short, fine gauge needle placed just below the skin surface is an extremely common medical procedure. Most often this procedure is used to administer a very small dose of lidocaine to produce a skin wheal of local anesthetic before the introduction of a larger more painful needle or instrument through that area of skin. This is frequently done prior to the insertion of a larger bore intravenous catheter. About 110 million such catheters alone are used annually, most of which would be facilitated by the prior use of an intradermal anesthetic skin wheal. Another occasion when the intradermal anesthetic skin wheal is used is prior to the introduction of a needle for a diagnostic radiologic procedure such as the X-ray needle localization of a breast mass. There are many other diagnostic and therapeutic medical procedures which routinely require the prior use of the intradermal injection of local anesthetic medication.

Another common form of hypodermic injection of medication is a subcutaneous injection using a slightly longer, fine gauge needle placed in the subcutaneous tissue between the skin and muscle. This procedure is commonly used, for example, to administer a standard dose of heparin in the prophylaxis of phlebitis.

Ordinarily, when an intradermal anesthetic skin wheal or a subcutaneous injection is administered, the practitioner uses a 1 cc tuberculin or insulin syringe with a fine gauge needle. The syringe is, of course, a piston within a cylindrical chamber made of glass or plastic. The local anesthetic or other medication must first be drawn up from a multidose vial, the ubiquitous air bubble tapped to the top of the syringe and ejected, the skin wheal administered, and the used syringe dangerously recapped or, alternatively, set aside unguarded, to be disposed of later. Needle guards for hypodermic needles have consisted of separate caps whose use may increase the likelihood of needle stick injury. Other needle guards attached to a conventional injection device or syringe require a separate action for their deployment. The disadvantages of the above technique, using the conventional syringe and needle, are as follows:

1. Using only a small amount of medication from a large vial may not be cost effective due to waste.
2. The multidose vial may be cross contaminated after frequent use and storage.
3. The drawing up of medication is time consuming and inconvenient.
4. The possibility exists of transmitting infection from inadvertent needle stick from the unguarded used needle.

The solution to the disadvantages above is to make available the proposed intradermal or hypodermic injection device, containing a prepackaged unit dose of medication, attached to a needle with an integral needle guard which is deployed by the same easy action by which the medication is administered.

SUMMARY OF THE INVENTION

The intradermal injection device is comprised of a fine gauge short needle and sealed hub enveloped by a tear-drop shaped flexible elastic bulb reservoir containing a measured unit dose of the desired medication (typically 1% lidocaine) to be administered intradermally. In addition, an easily deployed needle cover or needle guard is an integral part of the device. The needle guard is a hard bead perforated by the needle such that the bead surrounds and slides over the needle and is attached by its back rim to the leading edge of the bulb. In the charged condition the needle is exposed and the bulb reservoir is full, containing the measured dose of medication. Using the back of the needle hub as a convenient handle, the needle is inserted intradermally. The bulb reservoir is then squeezed or pinched between the thumb and forefinger, discharging the measured unit dose of medication through a communicating passage into the needle hub and out through the needle, the back end of the hub being sealed. As the needle is withdrawn from the skin, by the same action pressure is continued between the thumb and forefinger forcing, by wedge action, the sliding needle guard over the end of the needle. Simultaneously, the needle is displaced laterally into a recess or blind passage in the needle guard from which it will not protrude, affording a measure of protection from inadvertent needle sticks to the user after the needle guard is so deployed. The lateral displacement of the needle tip into the recess or blind passage of the needle guard is achieved by an asymmetry inherent in the design. This asymmetry may be incorporated into the design by a number of different design mechanisms described later. The needle tip is kept in the recess or blind passage by the elastic recoil of the bulb. Even if the needle guard is advanced and relaxed again it will continue to fall into the recess due to the inherent asymmetry in the design.

A hypodermic injection device is a longer needle variation. In order to accomplish subcutaneous or intramuscular injection a longer needle is necessary. This requires a modification in the design to allow the sliding bead needle guard to extend over the longer needle. The modification comprises an appropriate extension of the back edge of the bulb in the form of a continuous sleeve which, with the needle guard in the undeployed state, folds backward or invaginates over itself as an intussusception. With the continued squeezing or pinching action used to discharge the medication as the needle is withdrawn the invaginated sleeve will extend to allow the needle guard to slide over the longer needle. The needle tip is again displaced laterally, by asymmetry of design, into the recess or blind passage.

DETAILED DESCRIPTION OF THE PREFERRED EMBODIMENTS

Figure 1:
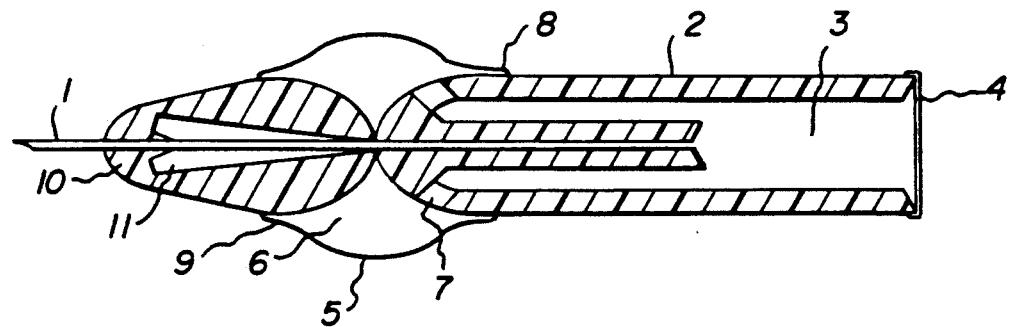
FIG. 1 shows an intradermal injection device or short needle hypodermic injection device, enlarged cross section (scale 3×), either side or top view which are the same, as the device drawn has rotational symmetry about the needle axis.

FIG. 1 shows an intradermal injection device or short needle hypodermic injection device with a bulb reservoir, containing a prepackaged unit dose of medication and an integral needle guard. The device comprises a short, fine gauge (such as 30 gauge) hollow hypodermic needle 1 connected to a hollow needle hub 2. The back of the hub is sealed by seal 4 at manufacture after the prepackaged unit dose of the desired medication has been added. The needle and hub are enveloped by a tear-drop shaped flexible elastic bulb 5 defining bulb reservoir 6 containing the measured unit dose of the medication to be administered intradermally. The back edge of the bulb 8 is connected to the needle hub and the bulb reservoir communicates through the communicating passage 7 between the bulb reservoir and the hub chamber 3. In addition, an easily deployed needle cover or needle guard 10 is an integral part of the device. The needle guard is a hard bead perforated by the needle such that the bead surrounds and slides over the needle and is attached by its back rim to the leading edge 9 of the bulb. In the charged condition the needle is exposed and the bulb reservoir is full, containing the measured dose of medication. Using the back of the needle hub as a convenient handle, the needle is inserted intradermally. The bulb reservoir is then squeezed or pinched between the thumb and forefinger, discharging the measured unit dose of medication through a communicating passage into the chamber of the needle hub and out through the needle, the back end of the hub being sealed. As the needle is withdrawn from the skin, by the same action pressure is continued between the thumb and forefinger, forcing by wedge action the sliding needle guard over the end of the needle. Simultaneously, the needle is displaced laterally into a recess or blind passage 11 in the needle guard from which it will not protrude, affording a measure of protection from inadvertent needle sticks to the user after the needle guard is so deployed. The lateral displacement of the needle tip into the recess or blind passage is achieved by asymmetry inherent in the design. The needle tip is kept in the recess or blind passage by the elastic recoil of the bulb. Even if the needle guard is advanced and relaxed again it will continue to fall into the recess due to the inherent asymmetry in the design. The asymmetry of the device which produces the lateral displacement of the needle into the recess may be achieved in any number of ways. First, the recess or blind passage may be along the axial line of the device while the needle perforates the needle guard off center. Second, the thickness of the bulb material may be asymmetrical, causing asymmetrical elastic recoil on the needle guard thus displacing it laterally with respect to the needle. Third, the force applied between the thumb and finger are asymmetrical enough to cause lateral displacement of the needle into the recess or blind passage of the needle guard. Material for construction can be of polyvinylchloride except for the steel needle.

Figure 2:
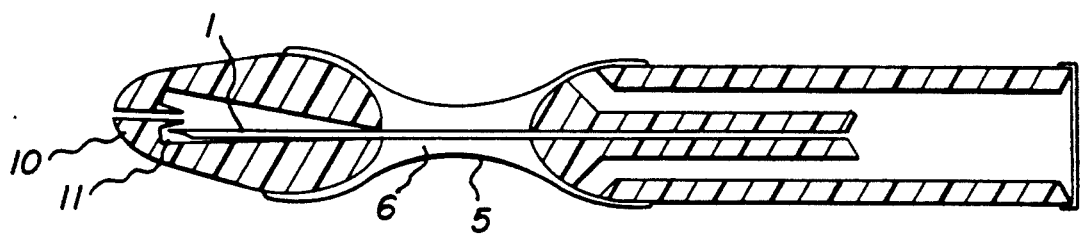
FIG. 2 shows the same intradermal injection device (scale 3×) of FIG. 1 in the discharged state with the needle guard deployed.

FIG. 2 shows the intradermal injection device in the discharged state with the needle guard 10 deployed and engaged over the needle 1, and the bulb 5 deflated with the bulb reservoir 6 discharged, and the needle displaced laterally in the recess 11.

Figure 3:
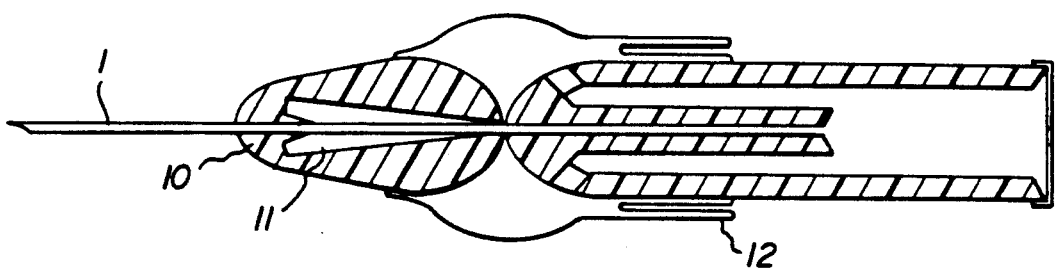
FIG. 3 shows the longer needle variation, the hypodermic injection device, enlarged cross section (scale 3×) either side or top view, as the device drawn has rotational symmetry about the needle axis.

FIG. 3 shows a longer needle hypodermic injection device. In order to accomplish subcutaneous or intramuscular injection, a longer needle is necessary. This requires a modification in the design to allow the sliding needle guard 10 to extend over the longer needle 1. The modification comprises an appropriate extension of the back edge of the bulb in the form of a continuous flexible sleeve 12 which, in the undischarged state of the device, with the needle guard in the undeployed state, folds backward or invaginates over itself as an intussusception. With the continued squeezing or pinching action used to discharge the medication as the needle is withdrawn, the invaginated sleeve will extend to allow the needle guard to slide over the longer needle. The needle tip is again displaced laterally, by asymmetry of design, into the recess or blind passage 11.

An additional variation (not illustrated) can exist wherein the bulb reservoir does not envelope the needle and hub, but still communicates with the hub chamber. The bulb may be either attached to or in juxtaposition with the needle guard or an extension thereof, such that when the medication is dispensed by squeezing or pushing on the bulb the needle guard is pushed forward into the deployed state.

While the injection device of the present invention may be offered for sale with the bulb reservoir 6 provided with a prepackaged dose of a predetermined amount of medication, the device may also be offered for sale with the bulb reservoir empty. The medication may then be inserted into the bulb reservoir by a separate syringe just prior to injection. The dose may thus be varied and this method can be valuable for medications having a short useful life or when there are other restrictions on the use of a particular medication.

While preferred embodiments of the present invention have been shown and described herein, such embodiments are provided by way of example only. Numerous variations, changes and substitutions will occur without departing from the invention herein. Accordingly, I intend that the invention be limited only by the spirit and scope of the appended claims.

I claim:

1. An intradermal or hypodermic injection device comprised of:

a chamber within a hollow hub attached to a hollow hypodermic needle means, said chamber being sealed at a back end by a seal attached to said hub means;

a flexible elastic bulb attached at one end to said hub and enveloping all but a exposed tip end of said needle means to form a reservoir means for holding a prepackaged dose of medication, which reservoir means communicates with the chamber of said needle means and said hub, through a communicating passage in said hub, the contents of said reservoir means dispensed by way of said communicating passage to said chamber of said hub through said hollow needle means by action of squeezing of said bulb;

a needle guard, attached to the leading edge of said bulb, perforated by the exposed tip end of said needle means in the undischarged state of the device, which needle guard slides over the tip end of said needle means deployed by the same squeezing action used to dispense the medication of said reservoir means.

2. The intradermal injection device as described in claim 1 in which said reservoir contains a prepackaged medication.

3. The injection device as described in claim 1 in which the needle guard is provided with a recess comprising a blind passage means to contain said needle tip by which the tip of said needle will not protrude after said needle guard has been deployed, said needle means kept in said recess by elastic recoil of said bulb in a discharged state.

4. A hypodermic injection device comprised of
 a chamber within a hollow hub attached to a hollow hypodermic needle means, said chamber being sealed at a back end by a seal attached to said hub;
 a flexible elastic bulb attached at one end to said hub and enveloping all but a exposed tip end of said needle means to form reservoir means for holding a prepackaged dose of medication, which reservoir means communicates with the chamber of said needle means and said hub, through a communicating passage in said hub, the contents of said reservoir means dispensed by way of said communicating passage to said chamber of said hub through said hollow needle means by action of squeezing of said bulb;
 a needle guard, attached to the leading edge of said bulb, perforated by the exposed tip end of said needle means in the undischarged state of the device, which needle guard slides over the tip end of said action used to dispense the medication of said reservoir means;
 an extension of said bulb in the form of a continuous flexible sleeve folding back over itself in the undischarged state of the device, which, when the contents of the bulb reservoir are dispensed, extends to allow said needle guard to slide over a longer needle means.

5. The hypodermic device as described in claim 4 in which said reservoir contains a prepackaged medication.

6. The injection device as described in claim 4 in which the needle guard is provided with a recess comprising a blind passage means to contain said needle tip by which the tip of said needle will not protrude after said needle guard has been deployed, said needle means kept in said recess by elastic recoil of said bulb in a discharged state.

* * * * *